United States Patent [19]

ten Hoff et al.

[11] Patent Number: 5,406,951
[45] Date of Patent: Apr. 18, 1995

[54] INTRA-LUMINAL ULTRASONIC INSTRUMENT

[76] Inventors: Harm ten Hoff, Albert Camus Plaats 225, Rotterdam; Gerard Faber, Hildelaan 12, 2645 NW Delfgauw; Gerrit Jan van Dijk, Bagdadstraat 6, Delft, all of Netherlands

[21] Appl. No.: 137,578
[22] Filed: Oct. 15, 1993
[51] Int. Cl.⁶ .................................. A61B 8/12
[52] U.S. Cl. .................... 128/662.06; 128/660.1
[58] Field of Search .................. 128/660.07, 662.06, 128/660.03; 264/23; 73/633; 310/334; 29/25.35

[56] References Cited

U.S. PATENT DOCUMENTS

| | | | |
|---|---|---|---|
| 4,734,611 | 3/1988 | Granz | 310/324 |
| 4,914,565 | 4/1990 | Schnoeller et al. | 367/164 |
| 4,951,677 | 8/1990 | Crowley et al. | 128/662.06 |
| 5,002,058 | 3/1991 | Martinelli | 128/662.06 |
| 5,070,882 | 12/1991 | Bui et al. | 128/662.06 |
| 5,143,089 | 9/1992 | Alt | 128/642 X |
| 5,240,003 | 8/1993 | Lancee et al. | 128/662.06 |
| 5,240,004 | 8/1993 | Walinsky et al. | 128/662.06 |
| 5,268,082 | 12/1993 | Oguro et al. | 204/282 |
| 5,271,402 | 12/1993 | Yeung et al. | 128/662.06 |
| 5,340,510 | 8/1994 | Bowen | 264/22 |

*Primary Examiner*—Francis Jaworski
*Attorney, Agent, or Firm*—Thomas R. Vigil; James P. Hanrath

[57] ABSTRACT

The intra-luminal ultrasonic instrument includes a catheter comprising a body, a flexible rotatable drive shaft within the body, an opalescent tip coupled to the flexible rotatable drive shaft having a distal end and a distal end portion adapted to be introduced into a lumen and a proximal portion, and a transducer mounted in the tip for rotation at a selected rpm, the catheter having a diameter no greater than 3 millimeters, the flexible rotatable drive shaft having a central longitudinal channel containing coaxial cable cooperative with conductors to connect the transducer to a source of energy for energizing the transducer to produce and supply sound waves, and the transducer having a top surface comprising a matching layer of a conductive polymer set upon a piezo plate.

15 Claims, 6 Drawing Sheets

INTRA-LUMINAL ULTRASONIC INSTRUMENT

BACKGROUND OF THE INVENTION

1. Field of the Invention

The present invention relates to a disposable intra-luminal ultrasonic instrument which includes an ultrasonic catheter that has a sound wave transducer therein for directing the sound waves outwardly into tissue and for receiving echo sounds to the transducer for transmission to a visual display which displays an ultrasound picture of the tissue whereby one can determine the makeup or construction of the tissue, e.g., hard or soft. The present invention also relates to a drive shaft used in such an instrument for rotating a specialized transducer.

2. Description of the related art including information disclosed under 37 CFR Sections 1.97-1.99.

Heretofore it has been proposed in Dutch Patent Application No. 87.00632 to provide a catheter having a catheter tip with a rotatable acoustic mirror therein or a rotatable tip having an acoustic mirror therein. A flexible shaft extends from the rotatable acoustic mirror to the proximal end of the catheter where it is driven by a suitable motor situated outside the catheter. A transducer is mounted in the catheter tip opposite the rotatable acoustic mirror. Rotation of the acoustic mirror within the tip or the tip portion having the mirror thereon causes high frequency ultrasonic vibrations or sound waves emitted by the transducer to be emitted in different directions in a rotating path and the echoes of the sound waves are received by the acoustic mirror and thence by the transducer for transmission to a visual display whereby a picture can be created of the space around the catheter tip which may contain tissue or a stenotic buildup in a vessel.

A problem with the instrument having the catheter described above is that the flexible drive shaft is fairly long, i.e., at least as long as the catheter itself. With this arrangement, it is difficult to supply a torsion free rotational force through the flexible drive shaft and to drive such a long flexible drive shaft for extended periods of time without malfunctioning.

It has been suggested in Dutch Patent Application No. 87.00632 to provide a turbine driven by fluid at or near the catheter tip with the turbine having a short drive shaft coupled to the rotatable acoustic mirror.

Heretofore it has been proposed in European Patent Application Publication No. 0 139 574 to provide an endocavity probe having a motor mounted in the distal end of one embodiment of the probe. The motor rotates a mirror which reflects signals emitted by a transducer.

This probe is utilized in examining organs and the like of a body. The probe is somewhat bulky in shape and size, is intended for insertion in body cavities, is not suitable for insertion inside veins and/or arteries and does not teach a motor having stator coils mounted on a flexible circuit board and having a diameter no greater than 3 millimeters mounted in a catheter tip.

As will be described in greater detail below, the present invention in part provides an intra-luminal ultrasonic instrument having a flexible drive shaft and a transducer with improved performance characteristics avoiding resort to special turbines or motors.

A number of ultrasonic instruments for the examination and/or treatment of blood vessels have been previously proposed. Examples of these previously proposed instruments are disclosed in the following United States Patents, the disclosures of which are incorporated herein by reference:

| Patentee | U.S. Pat. No. |
| --- | --- |
| Kondo et al. | 4,572,201 |
| Yock | 4,794,931 |
| Pope et al | 4,889,757 |
| Prodian et al | 4,917,097 |
| Yock | 5,000,185 |
| Lum et al | 5,003,238 |
| Passafaro | 5,010,886 |
| Yock et al | 5,029,588 |
| Bom et al | 5,176,141 |
| Lancee et al | 5,240,003 |

SUMMARY OF THE INVENTION

According to the present invention, there is provided an intra-luminal ultrasonic instrument which includes a catheter comprising a body, a flexible rotatable drive shaft within said body, an opalescent tip coupled to said flexible rotatable drive shaft having a distal end and a distal end portion adapted to be introduced into a lumen and a proximal portion, and a transducer mounted in said tip for rotation at a selected rpm, said catheter having a diameter no greater than 3 millimeters, said flexible rotatable drive shaft having a central longitudinal channel containing coaxial cable cooperative with conductors to connect said transducer to a source of energy for energizing the transducer to produce and supply sound waves, and said transducer having a top surface comprising a matching layer of a conductive polymer set upon a piezo plate.

The present invention provides for a compact, inexpensive intra-luminal ultrasonic instrument having a low twisting, high performance flexible rotatable drive shaft and a transducer with improved performance characteristics. The flexible drive shaft achieves maximum rotational transmission with high angular fidelity over a length of approximately 1.5 meters while assuring optimal flexibility in catheters using an outer diameter of approximately 1.3 mm. The transducer preferably is elliptical shaped which yields improved beam properties through reduced side lobes of the beam in comparison with circular transducers in the same environment. The transducer is further provided with the scanning angle of 10° (±10%) relative to a line perpendicular to the catheter axis in order to achieve maximum transducer surface with maximum sensitivity in a reduced volume.

The intra-luminal ultrasound instrument of the present invention possesses blood compatibility, sonolucent properties, and is inert under normal medical regimes such as sterilization processes.

Additional features and advantages of the present invention will become apparent to those skilled in the art from the following description and the accompanying figures illustrating the preferred embodiment of the invention, the same being the present best mode for carrying out the invention.

DESCRIPTION OF THE PREFERRED EMBODIMENT

Figure 1:
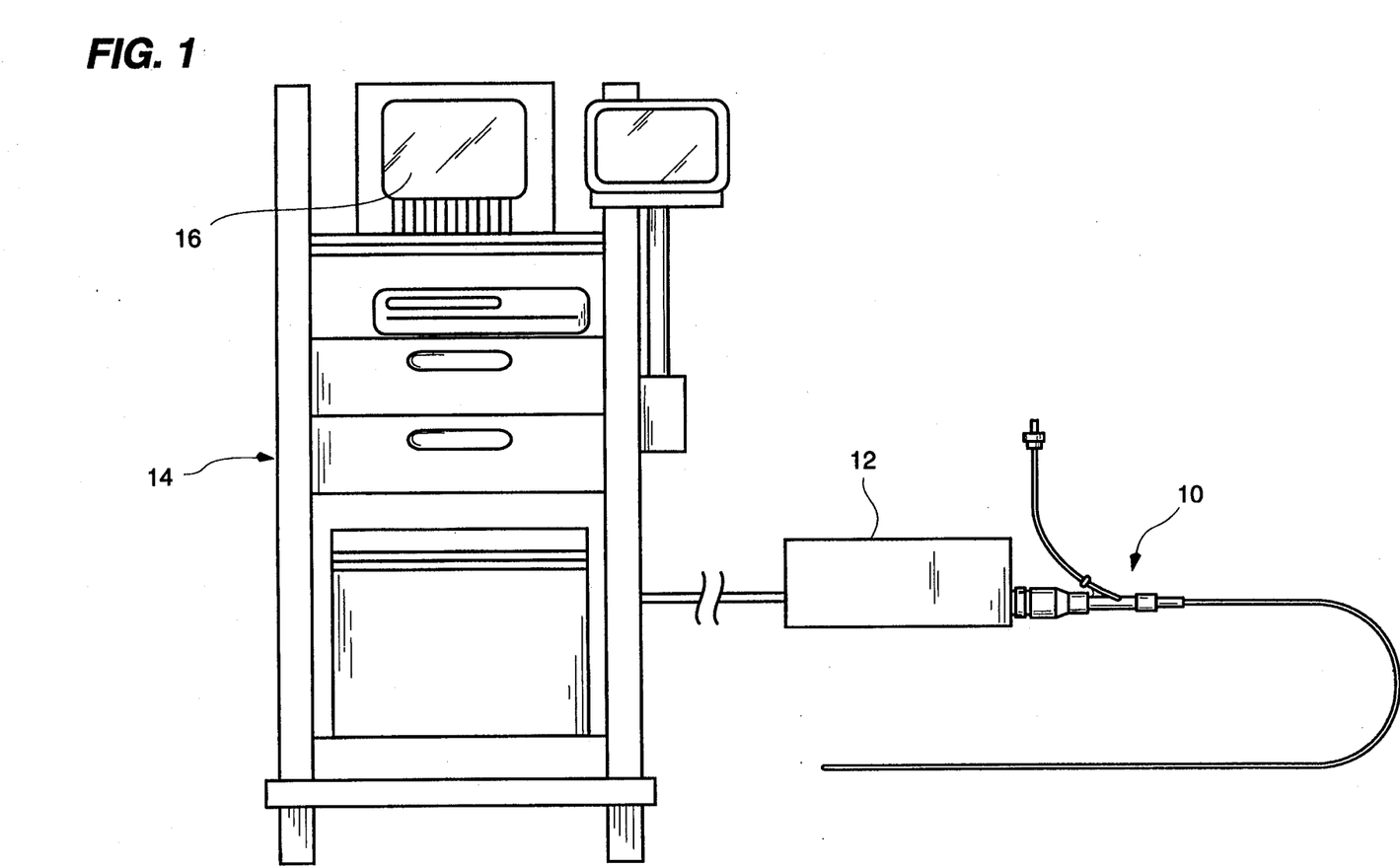
FIG. 1 is front view of the intra-luminal ultrasonic instrument of the present invention joined to an electrical energy source cooperative with a console assembly having a visual display unit where an ultrasound image is produced by a transducer of the ultrasonic instrument.

Referring now to the Figures in greater detail, there is illustrated in FIG. 1 an intra-luminal ultrasonic instrument 10 constructed according to the teachings of the present invention coupled to an electrical power source 12 in communication with a console assembly 14 having a visual display unit 16. A transducer of the intra-luminal ultrasonic instrument 10 supplies a visual display of an ultrasound image of the space surrounding a catheter tip of the ultrasonic instrument and the material in that space.

Figure 4:
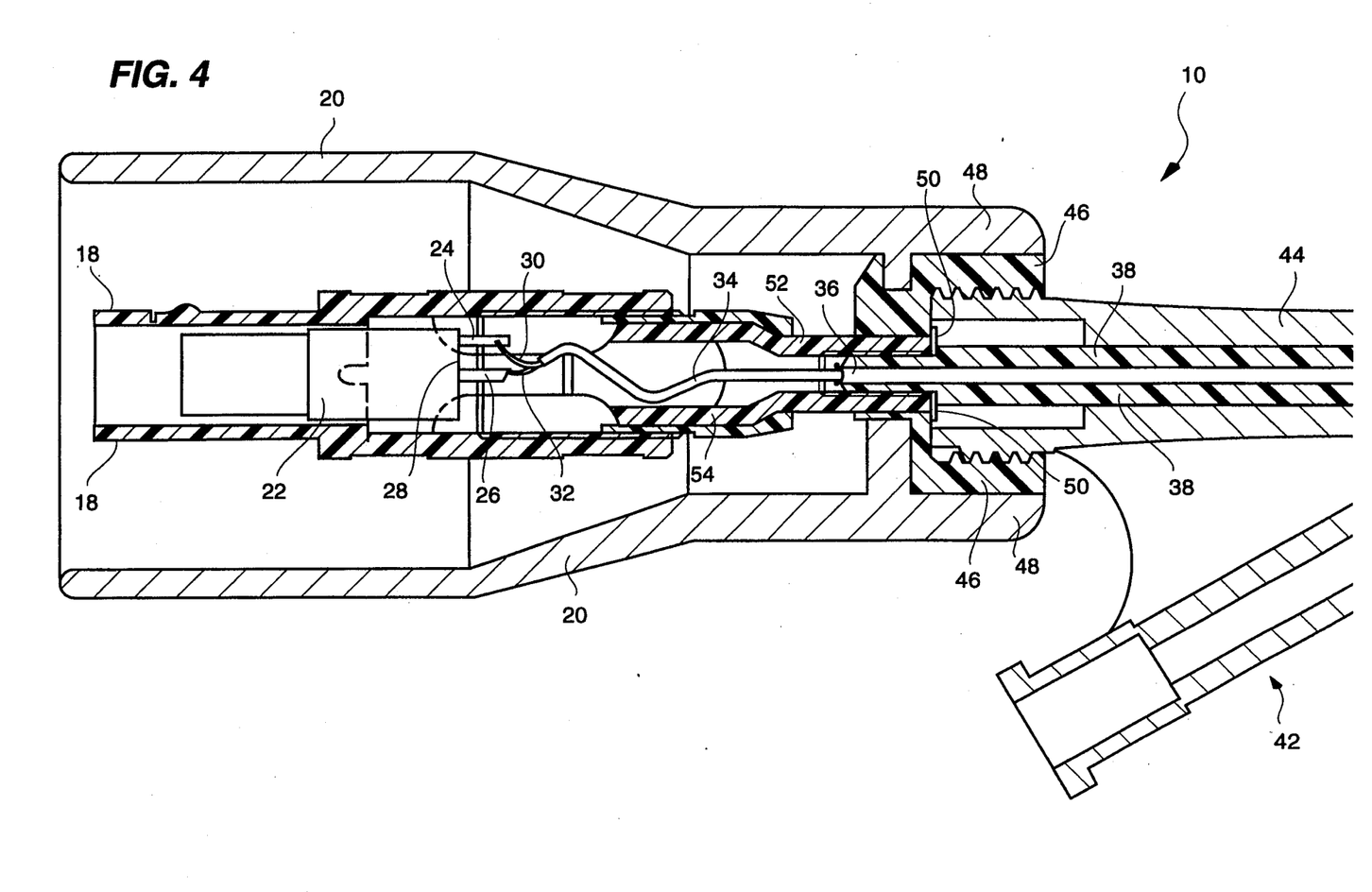
FIG. 4 is an enlarged cross-sectional view of the proximal end and part of the intermediate portion of the intra-luminal ultrasonic instrument of the present invention.
Figure 5:
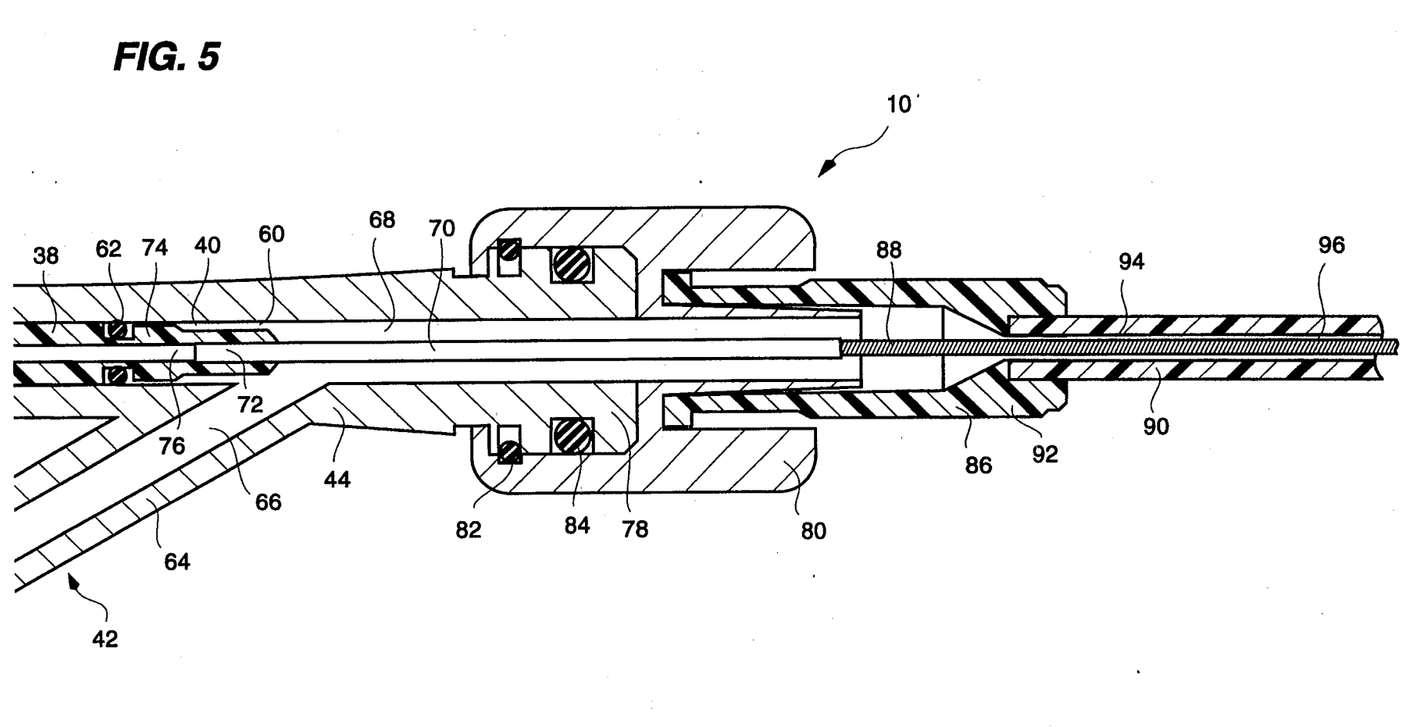
FIG. 5 is an enlarged cross-sectional view of part of the intermediate portion and part of the distal portion of the intra-luminal ultrasonic instrument of the present invention.

In FIGS. 4 and 5 there is illustrated an enlarged cross-sectional view of an intra-luminal ultrasonic instrument constructed according to the teachings of the present invention. FIG. 4 shows the proximal portion and part of the intermediate portion of the instrument and FIG. 5 shows the remaining part of the intermediate portion and part of a distal portion of the instrument.

Referring to FIG. 4 there is shown electrical plug 18 housed within electrical connector protector body 20 which is capable of making a detachable electrical connection with an electrical energy source. Housed within electrical plug 18 is a cylindrical coupling element 22 having connection arms 24 and 26 longitudinally extending from distal end 28 of the cylindrical coupling element for connection with proximal ends of outer conductor coax 30 and inner conductor coax 32 respectively of coaxial electrical cable 34. Coaxial electrical cable 34 extends within spacer tube 36 housed within a longitudinal channel of drive shaft connector 38 which in turn is housed within longitudinal cavity 40 of proximal portion 42 of Y-connector 44 (see also FIG. 5). Proximal end portion 42 of Y-connector 44 is adapted to fit within bearing 46 affixed within the distal end 48 of electrical connector protector body 20. Washer 50 separates drive shaft connector 38 from connector adaptor 52. Drive-turn sheath 54 cooperates with a plurality of teeth 56 of turn element 58 housed within connector adaptor 52 to provide rotation of turn element 58, drive shaft connector 38, and a cooperative flexible rotatable drive shaft hereinafter described.

Referring now to the intermediate portion of the ultrasonic instrument illustrated at FIGS. 4 or 5, drive shaft connector 38 longitudinally extends within the longitudinal channel 60 of proximal portion 42 of Y-connector 44 and terminates at O-ring 62. Y-connector 44 has a branch arm 64 providing an access port 66 into stem portion 68 of Y-connector 44. Liquids, dye injections, pressure measurements, and other access necessitating procedures may utilize access port 66 of branch arm 64 to supply the ultrasonic instrument 10 with appropriate liquid, dye injection or other material. Connector tube 70 having a proximal end 72 set within stabilizing member 74 is centrally longitudinally aligned within the longitudinal chamber 40 of stem portion 68 of Y-connector 44 such as to receive therein the distal end 76 of spacer tube 36. Affixed to the distal end portion 78 of Y-connector 44 is male luer 80 which encloses bearing 82 and O-ring 84 over distal end portion 78. Female luer 86 is distally matingly secured to male luer 80. Flexible rotatable drive shaft 88 extends longitudinally from connector tube 70 into strain relief 90 which is longitudinally centrally connected within distal end 92 of female luer 86. Strain relief 90 houses the proximal end portion 94 of catheter shaft 96 within it. Catheter shaft 96 extends distally longitudinally from strain relief 90.

Catheter shaft 96 may be in the form of a thin flexible tube made of a suitable disposable material, e.g., a plastic material which forms part of a disposable intra-luminal ultrasonic instrument 10. The outer diameter of the shaft is not more than 3 millimeters and will, for example, be 0.62 millimeters if the instrument is used for the examination and/or treatment of coronary vessels.

Figure 3:
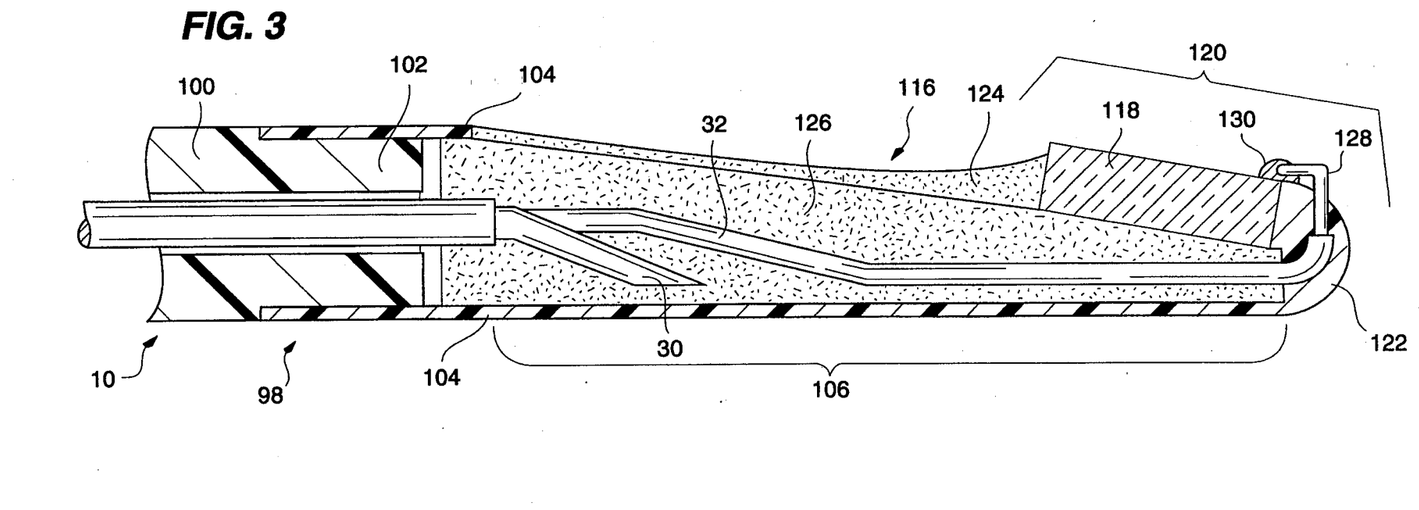
FIG. 3 is an enlarged vertical sectional view of the drive shaft and transducer assembly, is taken along line 2—2 of FIG. 2, and shows coaxial cable providing an electrical connection to the transducer.

Referring now to FIG. 3 illustrating in cross section the distal end 98 of the ultrasonic instrument 10 there is shown the distal end portion 100 of flexible rotatable drive shaft 88 which terminates in a reduced in diameter distal end 102. This reduced in diameter distal end 102 is securely connected within transducer mounting tube 104 having a transducer assembly 106 extending longitudinally from the elongated axis of flexible rotatable drive shaft 88.

Flexible rotatable drive shaft 88 and the transducer assembly 106 connected therewith can be driven at an rpm between 600 and 4,000 rpm, e.g., 1,200 rpm, 1,800 rpm, 3,000 rpm or 3,600 rpm up to but not limited to 6,000 rpm.

The flexible rotatable drive shaft 88 may be operated at a speed of rotation synchronized with a raster across a visual display to which the echoes of the sound waves received by the transducer are supplied, and the rotation of the transducer may be oriented with respect to the raster.

Flexible rotatable drive shaft 88 possesses design characteristics that allows it to achieve maximum rotational transmission with high angular fidelity over a length of approximately 1.5 meters, while assuring optimal flexibility in catheters using a outer diameter of approximately 1.3 mm. Flexible rotatable drive shaft 88 performs its function with a constant error angle smaller than 10 degrees, a stochastic error angle smaller than 0.5 degrees in absolute value, and a periodic error angle smaller than 20 degrees peak to peak. These values are achieved in both driving directions. The drive shaft properties at the basis of above performance are: a ratio bending rigidity (BR) versus torsional rigidity (TR) lower or equal to 0.015, a bending rigidity lower or equal to $1.5 \times 10^{-6}$ Nm$^2$, and a torsional rigidity higher or equal to $100 \times 10^{-6}$ Nm$^2$.

A drive shaft with the above operating characteristics is obtained by the design and assembling process relative to the flexible rotatable drive shaft 88. Specifically, drive shaft 88 contains a multiple filament inner round wire spiral coil and outer round wire spiral coil of 8 filaments (minimally) per spiral. During the assembling process the inner and outer spiral exhibit an interference fit (IF). The outer diameter of the relaxed inner spiral is larger than the internal diameter of the outer spiral in relaxed form. After the assembling process the succeeding coils are not necessarily in contact.

The drive shaft 88 is produced with the following methods and characteristics:

the spirals are separately wound around separate mandrils on a coil winding machine (CWM) with Mandril sizes of for the Outer spiral: 0.546 mm±0.5%±0.003 mm and for the Inner spiral: 0.483 mm±0.5%±0.003 mm;

the tensile force of the spiral filament during the process is for the outer spiral: 2N±0.5% and for the inner spiral: 2N±0.5%;

the filament has a size of a round cross sectional diameter of 75 um±0.3%±0.003 mm;

the tensile force on the mandrils during the coil winding process are for the outer mandril: 60N±0.5% and for the inner mandril: 60N±0.5%;

the mandril rotational speed during the coil winding equals for the inner spiral: 700 rpm±0.5% and for the outer spiral: 680 rpm±0.5%;

the linear carriage speed during the coil winding equals for the inner spiral: 0.004 m/s±0.5% and for the outer spiral: 0.004 m/s±0.5%;

the wound spirals are soldered to the mandrils in such a way that results in inner and outer mandril spiral combinations with an outer diameter of inner combination: 0.635 mm±0.5% and outer combination: 0.648 mm±0.5.%;

the assembly of above mentioned spirals is such that a relaxation of the outer spiral takes place by cutting the solderings resulting in a larger outer diameter of 0.796 mm ±0.5% and an inner diameter of 0.5 mm±10% the inner combination under tension is then introduced;

subsequently the solderings of the inner spiral are cut, and care is taken that the above mentioned interference fit is uniformly distributed over the total length;

the mandril is removed from the inner spiral and both ends of the drive shaft are soldered;

after the production has taken place the following quality controls are undertaken: visual inspection relative to winding/coil irregularities and the product's straightness, measurement of torsional rigidity (TR) within the specifications above, and measurement of bending rigidity (BR) within the specifications above.

These production parameters adequately determine the functional performance of the drive shaft. The combination of mandril sizes and filament elasticity adequately determines the potency of the interference fit necessary for the desired performance.

Figure 6:
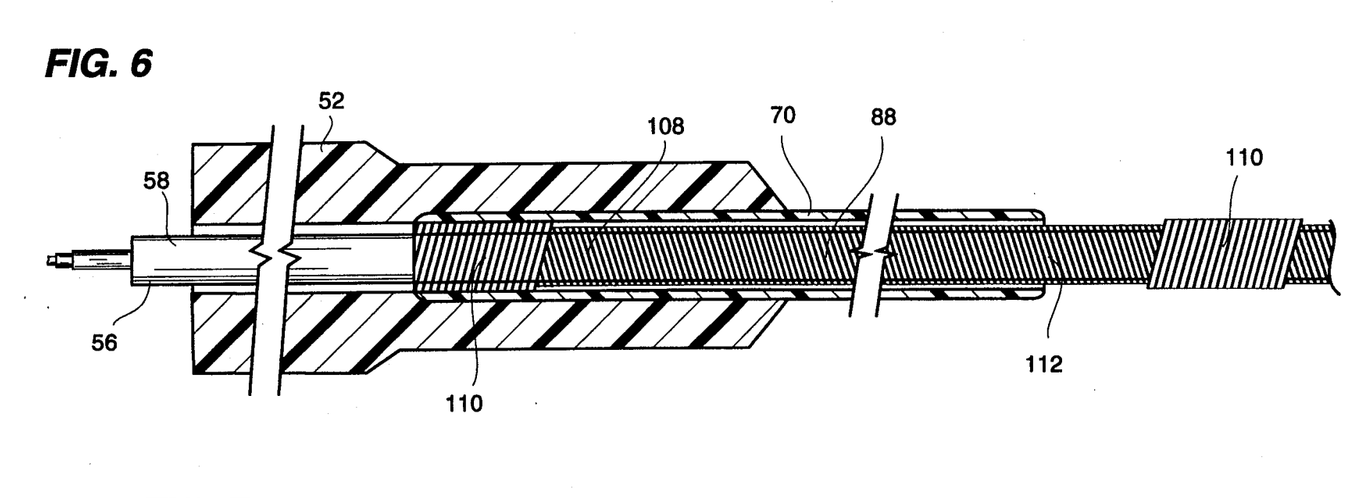
FIG. 6 is an enlarged cross-sectional view of a flexible drive shaft of the intra-luminal ultrasonic instrument constructed according to the teachings of the present invention.
Figure 7:
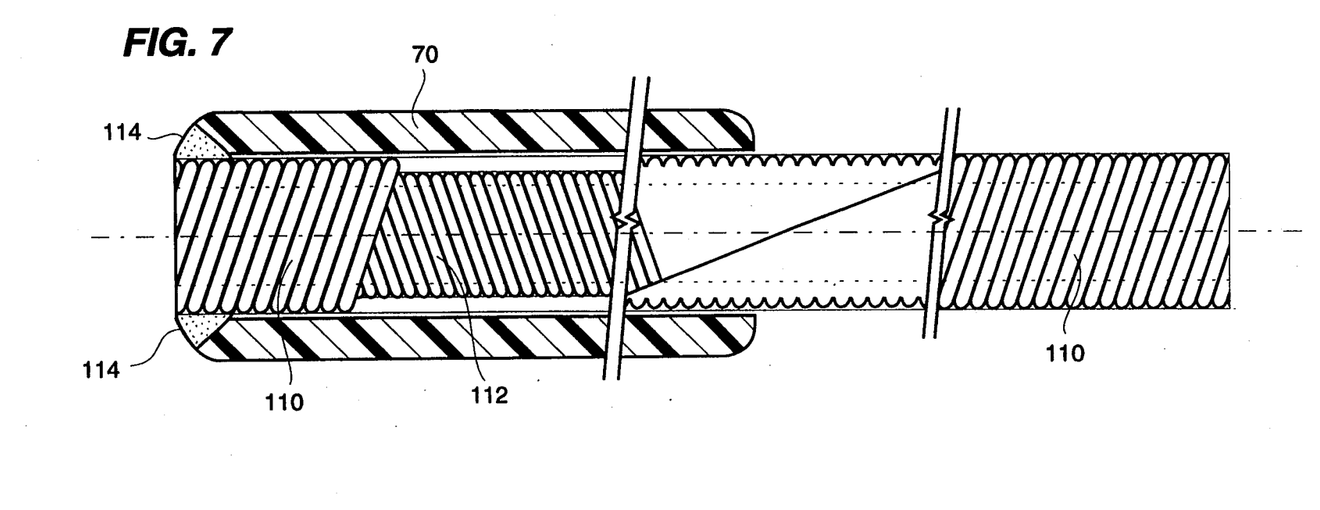
FIG. 7 is an enlarged cross-sectional view showing multiple cross-sections of the flexible drive shaft of the intra-luminal ultrasonic instrument of the present invention and shows round wires forming inner and outer coils of the drive shaft.

FIG. 6 shows an enlarged partial cross-sectional view of flexible rotatable drive shaft 88. Proximal end 108 of drive shaft 88 is affixed within connector tube 70 which is secured within connector adaptor 52. Housed within connector adaptor 52 is a turn element 58 having a plurality of gear teeth 56 at its external surface cooperative with drive-turn sheath 54 (shown at FIG. 4) to provide rotation of turn element 58, drive shaft connector 38 and flexible rotatable drive shaft 88. As better observed in FIG. 7, flexible rotatable drive shaft 88 is comprised of a multiple filament outer spiral coil 110 wrapped around inner spiral coil 112. The inner diameter of the outer spiral coil 110 is 0.64 mm. The outer diameter of the inner spiral coil 112 is 0.702 mm. The inner and outer spiral coils may be made of round wire having a dimension of 0.003±0.0001 inches with a tensile strength of 325,000±5,000 psi. The distal end of the inner and outer spiral coils 112 and 110 respectively are secured together for a length of approximately 1–2 mm and no holes in brazing at the grinded end are allowed. Brazing paste 114 is applied around the entire inner circumference between connection tube 70 and connector adaptor 52. The proximal end of the inner and outer spiral coils 112 and 110 respectively are secured together for the length of a minimum of 2 mm to a maximum of 4 mm. The outer surface of the drive shaft is smooth and free of bends or kinks. After assembly the inside diameter which remains open of the drive shaft is a minimum of 0.04 mm through the total inner spiral coil.

Referring again to FIG. 3 transducer assembly 106 is joined to the reduced in diameter distal end 102 of the flexible rotatable drive shaft 88 at transducer mounting tube 104. Transducer assembly 106 comprises a catheter tip member 116 having a transducer 118 mounted at a distal portion 120 thereof. Ultrasonic radiation at critically selected frequencies is emitted and received by the transducer 118 which preferably is a piezo-ceramic element. If the ultrasound wave is reflected by an obstacle, such as an artery wall, when the catheter tip is mounted in an artery, the reflected or echoed signal so generated will be reflected or received by the transducer 118. The reflected sound waves are then supplied by the transducer 118 to a visual display where an ultrasound image of the space surrounding the catheter tip 116 and the material in that space can be displayed on a visual display. The operating frequency of the sound wave will determine the depth of field of this ultrasonic imaging.

It has been found that in the megahertz frequency range lower frequencies, e.g., below 10 megahertz, will provide a deeper depth of field but with low resolution which might not be satisfactory. On the other hand, it has been found that frequencies between 45 and 60 megahertz, while providing good resolution, result in a shallower depth of field. Accordingly, in the instrument 10 of the present invention the ultrasonic sound waves generated by the transducer 118 are generated by a frequency that is not greater than 60 megahertz and typically in the range of 15 and 45 megahertz, and preferably at approximately 30 megahertz for a good balance between depth of field and resolution.

It has been found that the frequencies used, particularly approximately 30 megahertz, results in an ultrasound picture having a depth of field of at least one-half inch ($\frac{1}{2}''$) with good resolution so that the makeup or constitution, e.g., hard calcified or soft fatting material, of the tissue or stenotic buildup being investigated can be determined.

The manner in which ultrasonic pictures can be formed of the space surrounding the catheter tip 116 with the aid of echoes or ultrasonic radiation is described in Dutch Patent Application No. 87.00632, the disclosure of which is incorporated herein by reference.

Transducer assembly 106 has the following characteristics:

The transducer is operated in an aqueous environment with the top surface thereof in direct contact with water. The top surface of the transducer comprises a matching layer of 11 um+/−10% thickness of a conductive epoxy polymer to achieve, by blending, high acoustic damping properties, specifically acoustic impedance of approximately 6 MRayls. The layer behind the matching layer is a piezo plate resonating at a desired center frequency ranging from 10 to 50 $MH_z$. Behind the piezo plate is a carrier, usually called backing, which is not blended, being a standard electrical conductive epoxy;

the backing of the transducer is of high impedance electrical conductive epoxy. While normal silver containing epoxies have acoustic damping factors of circa 10 dB/mm, this factor in the backing of the transducer of the present invention is greater than 15 dB/mm and approximates 33 dB/mm. The epoxy is a standard two component, non-toxic, product which is cured at low temperatures; typically 70° centigrade. The electrical conductive epoxy is of the same type with the addition of either gold, silver or carbon. These products are standard and available from a great variety of vendors, e.g. Epoxy Technology Inc., Ablestik, Tra-Con Inc.;

the transducer preferably uses high density ceramics to avoid electrical break-down at high frequencies with the specific density approximating 7 to $8 \pm 1000$ $kg/m^3$;

the transducer preferably is of an elliptical shape with a scanning tip configuration of 10 percent slanting relative to a line perpendicular to the catheter axis, in order to achieve maximum transducer surface with maximum sensitivity in a reduced volume. At the same time this shape yields improved beam properties through reduced side lobes of this beam as compared with a circular transducer in the same environment. The scanning angle of 10 degrees +/−10% is a compromise between an angle close to perpendicular to the catheter axis, giving a substantial dome reflection and multiple reverberations, and an angle of n degrees with the line perpendicular to the true catheter axis, causing a substantial loss of reflection/back scatter signal from the vessel wall structures as is predicted from the "de Kroon-effect";

the transducer holder is X-ray opalescent. The catheter tip's opalescence exactly defines the position of the cross sectional image plane under X-ray; and the transducer is cooled during the manufacturing process of the laser cutting. The heat affected zone is limited to less than 50 um from the laser beam in order to avoid severe depolarization. Coupling factor reduction is at least 50%.

Referring again to FIG. 3, transducer 118 is set in catheter tip 116 at a scanning angle of 10°±10% relative to a line perpendicular to the catheter axis. The transducer 118, comprising a matching layer and piezo plate as aforesaid, is bordered distally by rounded distal end cap 122 made of non-conductive material, proximally by non-conductive adhesive 124 and below by electrically conductive epoxy 126. The rounded distal end cap 122 of the transducer holder is covered with non-conductive epoxy in order to prevent damage to the catheter wall during rotation. Electrically conductive epoxy 126 supports the piezo plate and is a carrier or backing comprising a standard high impedance electrical conductive epoxy as previously described. Coaxial electrical cable 34 at its distal end has outer conductor coax 30 grounded by being imbedded in electrically conductive epoxy 126 while inner conductor coax 32 extends longitudinally into distal end cap 122 where it terminates into an electrode connection 128 which electrically communicates with transducer 118 by conductive epoxy 130.

Catheter tip 116 serving as a holder for the transducer assembly 106 is made of a material which is transparent to ultrasonic radiation or sound waves when the instrument is provided with transducer means for emitting ultrasonic radiation and for receiving the echoes of the emitted radiation.

Figure 2:
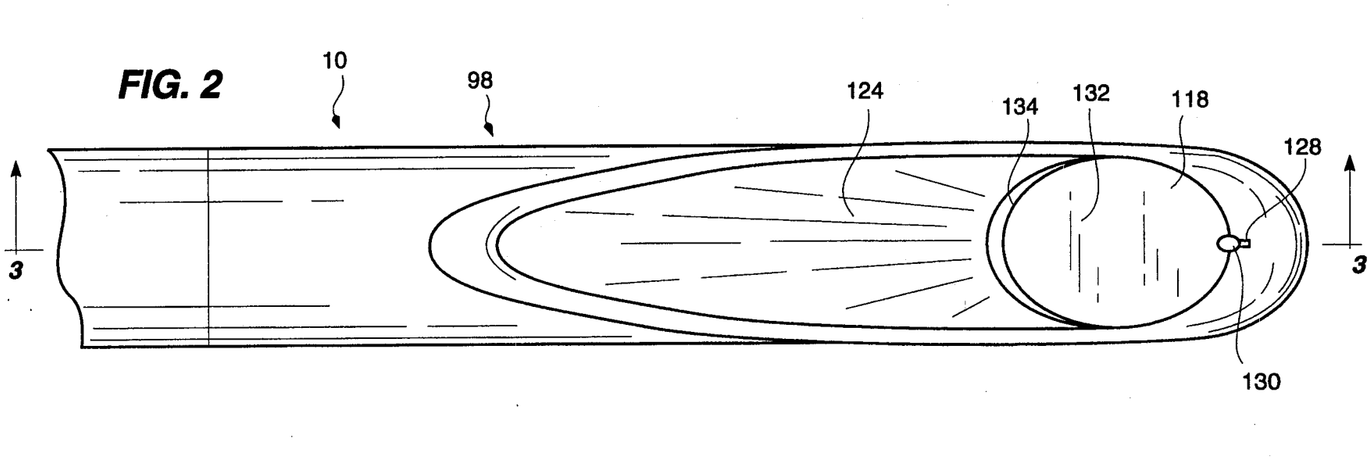
FIG. 2 is an enlarged top view of the transducer assembly connected to a flexible drive shaft of the intra-luminal ultrasonic instrument constructed according to the teachings of the present invention.

Referring now to FIG. 2 there is shown a top view of catheter tip 116 of the ultrasonic instrument 10 constructed according to the teachings of the present invention. Transducer 118 is shown to be elliptical in shape to yield improved beam properties. Alternatively, the transducer may have a hexagonal or octagonal form made by a diamond saw. This obviates the need for using numerically controlled machining equipment. Matching surface 132, the top surface of the transducer, is a conductive epoxy polymer of 11 um+/−10% thickness to achieve, by blending, high acoustic damping properties, specifically acoustic impedance of approximately 6 MRayls. Piezo plate 134 behind the matching layer, resonates at a desired center frequency ranging from 10 to 50 $MH_z$.

Catheter tip 116 is constructed to be flexible, but also stiff enough, so that the transducer can rotate freely. To be flexible enough the wall thickness of the catheter tip is between 0.10 and 0.05 mm. The catheter tip may be made from moulding mandrils and medical grade silicone tubing with swelling in a Freon bath and machine heatbonding for approximately 21 seconds at 180° C.

Figure 8:
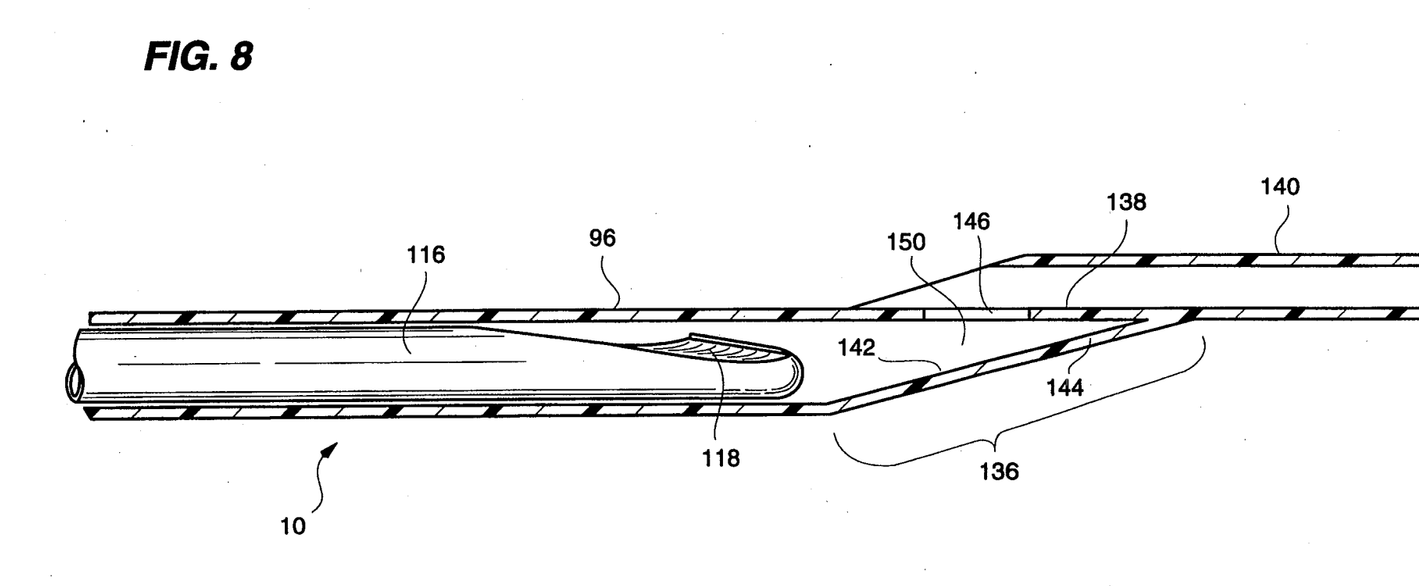
FIG. 8 is an enlarged cross-sectional view of the distal end of the catheter and image chamber tubing of the present invention and shows the same cooperative with a disjointed parallel guidewire tubing.

FIG. 8 illustrates a cross-section of the catheter shaft 96 having the catheter tip 116 of instrument 10 (shown in perspective) inserted therein. Catheter shaft 96 terminates in a image chamber portion 136 that shares a common wall 138 with guidewire tip tube 140 at its distal end. Common wall 138 preferably has a wall thickness of 0.198 0.005 mm while the wall thickness of guidewire tip tube 140 and image chamber tubing 142 is preferably minimally 0.087 mm. Guidewire tip tube 140 is disjointed from catheter shaft 96 and image chamber portion 136 such as to be adjacent thereto and sharing a portion of a common wall therewith but having a longitudinal center axis parallel spaced from the longitudinal center axis of the catheter. Guidewire tip tubing may accommodate appropriate guidewires suitable for various imaging and treatment procedures. Thus ultrasonic instrument 10 is adapted to receive a guidewire which can be moved through guidewire tip tubing 140 parallel spaced from the longitudinal axis of the instruments catheter body and which then can be extended longitudinally of the longitudinal axis of the guidewire tip tubing 140 which is parallel spaced from the longitudinal axis of the instruments catheter body. Guidewire tip tubing 140 is inclined at its proximal end and has at its distal end a circular end that is bevelled.

The catheter shaft 96 terminates in image chamber tubing 142 which is slanted at its distal end 144 to close against guidewire tip tubing 140.

A portion of the common wall between the imaging chamber tubing 142 and guidewire tip tubing 140 has a slit vent 146 which serves multiple functions in addition to aiding ultrasonic scanning. In this regard, liquid can be flushed forwardly from catheter shaft 96 through slit vent 146 in a forceful manner while slit vent 146, due to its thin/small size, prevents back leakage into the image chamber tubing 142 and the transducer assembly 106. Thus sonolucent transport is adequately taken care of while potential blood back-bleeding is minimalized.

The image chamber space 150 above the catheter tip 116 where the transducer 118 is located is primarily filled with a liquid before operating the instrument to ensure efficient acoustical operation of the instrument 10. The above referred to space can be pre-evacuated using vacuum techniques and liquid can be sucked into the space via slit vent 146.

The ultrasonic instrument of the present invention is constructed in a simple and inexpensive manner which allows the instrument to be a disposable instrument.

From the foregoing description it will be apparent that the ultrasonic instrument of the present invention has a number of advantages, some of which have been described above and others of which are inherent in the invention. Accordingly, the scope of the invention is only to be limited as necessitated by the accompanying claims.

We claim:

1. An ultrasonic instrument for the examination and/or treatment of blood vessels and similar lumina having a small transverse cross-section, said instrument including a catheter comprising a body, a flexible rotatable drive shaft within said body, an opalescent tip coupled to said flexible rotatable drive shaft having a distal end and a distal end portion adapted to be introduced into a lumen and a proximal portion, and a transducer mounted in said tip for rotation at a selected rpm, said catheter having a diameter no greater than 3 millimeters, said flexible rotatable drive shaft having a central longitudinal channel containing coaxial cable cooperative with conductors to connect said transducer to a source of energy for energizing the transducer to produce and supply sound waves, and said transducer having a top surface comprising a matching layer of a conductive polymer set upon a piezo plate.

2. The instrument of claim 1 wherein said matching layer has an acoustic impedance of approximately 6 MRayls.

3. The instrument of claim 1 wherein said piezo plate is set within an electrical conductive epoxy having an acoustic dampening factor greater than 15 dB/mm.

4. The instrument of claim 1 wherein said electrical conductive epoxy has an acoustic dampening factor of approximately 33 dB/mm.

5. The instrument of claim 1 wherein said catheter has a distal end cooperative with a flexible guidewire which can be moved through a tubular formation parallel spaced from the longitudinal axis of said catheter and which then can be extended longitudinally of the longitudinal axis of the tubular formation parallel spaced from the longitudinal axis of said catheter.

6. The instrument of claim 1 wherein said transducer is elliptical in shape.

7. The instrument of claim 1 wherein said transducer is mounted in said tip such as to establish a scanning angle of $10° \pm 10\%$ relative to a line perpendicular to the catheter axis.

8. The instrument of claim 1 wherein said flexible rotatable drive shaft has a ratio of bending rigidity versus torsional rigidity lower or equal to 0.015, a bending rigidity lower or equal to $1.5 *10^{-6}$ Nm$^2$, and a torsional rigidity higher or equal to $100 *10^{-6}$ Nm$^2$.

9. The instrument of claim 8 wherein said drive shaft comprises a multiple filament inner spiral coil and outer spiral coil of at least 8 filaments per spiral.

10. The instrument of claim 1 wherein said flexible rotatable drive shaft is operated at a speed of rotation synchronized with a raster across a visual display to which the echoes of the sound waves received by the transducer are supplied and the rotation of the transducer is oriented with respect to the raster.

11. The instrument of claim 1 wherein said transducer is constructed and arranged to generate sound waves at a frequency no greater than 60 megahertz.

12. The instrument of claim 1 wherein said transducer is constructed and arranged to generate sound waves at a frequency of between approximately 15 and 45 megahertz.

13. The instrument of claim 1 wherein said transducer is constructed and arranged to generate sound waves at a frequency of approximately 30 megahertz to obtain a sufficient depth of field with sufficient resolution to determine the makeup or constitution of the matter, such as tissue or plaque, in the space being investigated around the catheter tip.

14. The instrument of claim 1 being constructed to be a disposable intra-luminal instrument.

15. The instrument of claim 1 wherein said piezo plate is a high density ceramic having a specific density approximating 7 to $8 \pm 1000$ kg/m$^3$.

* * * * *